United States Patent
Ethirajan et al.

(10) Patent No.: US 10,640,597 B2
(45) Date of Patent: May 5, 2020

(54) METHOD FOR IMMOBILIZING MOLECULARLY IMPRINTED POLYMERS

(71) Applicants: IMEC VZW, Leuven (BE); Universiteit Hasselt, Hasselt (BE)

(72) Inventors: Anitha Ethirajan, Aachen (DE); Evelien Kellens, Leuven (BE)

(73) Assignees: IMEC VZW, Leuven (BE); Universiteit Hasselt, Hasselt (BE)

( * ) Notice: Subject to any disclaimer, the term of this patent is extended or adjusted under 35 U.S.C. 154(b) by 131 days.

(21) Appl. No.: 15/954,533

(22) Filed: Apr. 16, 2018

(65) Prior Publication Data
US 2018/0355089 A1    Dec. 13, 2018

(30) Foreign Application Priority Data

Jun. 13, 2017   (EP) ..................... 17175655

(51) Int. Cl.
*C08F 292/00*    (2006.01)
*G01N 33/53*    (2006.01)
*G01N 33/531*    (2006.01)
*G01N 33/543*    (2006.01)

(52) U.S. Cl.
CPC ......... *C08F 292/00* (2013.01); *G01N 33/53* (2013.01); *G01N 33/531* (2013.01); *G01N 33/54373* (2013.01); *G01N 2600/00* (2013.01)

(58) Field of Classification Search
CPC .......................... C08F 292/00; G01N 2600/00
See application file for complete search history.

(56) References Cited

U.S. PATENT DOCUMENTS

2014/0242605 A1*   8/2014   Eersels ............... G01N 25/18
                                                  435/7.1
2014/0336081 A1   11/2014   Nokihara et al.
2016/0178622 A1    6/2016   Peeters et al.

FOREIGN PATENT DOCUMENTS

EP      2772753 A1   9/2014
WO   2007/115541 A2  10/2007

OTHER PUBLICATIONS

Kellens, Evelien et al., "Improved Molecular Imprinting Based on Colloidal Particles Made from Miniemulsion: A Case Study on Testosterone and Its Structural Analogues", ACS Publications, Macromolecules, vol. 49, 2016, pp. 2559-2567.
European Search Report, European Patent Application No. 17175655.4 dated Nov. 27, 2017, 8 pages.
Lockett, Matthew R. et al., "Aldehyde-Terminated Amorphous Carbon Substrates for the Fabrication of Biomolecule Arrays", Langmuir, vol. 24, No. 17, Sep. 2, 2008, pp. 9198-9203.
Jan Grinsven, Bart, et al., "Heat-Transfer Resistance at Solid-Liquid Interfaces: A Tool for the Detection of Single-Nucleotide Polymorphisms in DNA", ACS NANO, vol. 6, No. 3, Feb. 22, 2012, pp. 2712-2721.

(Continued)

*Primary Examiner* — Ramsey Zacharia
(74) *Attorney, Agent, or Firm* — McDonnell Boehnen Hulbert & Berghoff LLP

(57) ABSTRACT

In a first aspect, the present disclosure relates to a method for immobilizing a molecularly imprinted polymer onto a substrate, comprising providing a substrate having an amorphous carbon surface; and grafting the molecularly imprinted polymer onto the amorphous carbon surface.

21 Claims, 4 Drawing Sheets

(56) References Cited

OTHER PUBLICATIONS

Shamsa, M. et al., "Thermal Conductivity of Diamond-Like Carbon Films", Applied Physics Letters, vol. 89, Oct. 20, 2006, pp. 161921-1-161921-3.
Peeters, M. et al., "Heat-Transfer-Based Detection of L-Nicotine, Histamine, and Serotonin Using Molecularly Imprinted Polymers as Biomimetic Receptors", Analytical and Bioanalytical Chemistry, vol. 405, 2013, pp. 6453-6460.
Li, Longfei et al., Preparation and Characterization of 5-Fluorouracil Surface-Imprinted Thermosensitive Magnetic Microspheres, Monatsh Chem, vol. 146, Nov. 15, 2014, p. 441-447.
Peeters, M. et al., "MIP-Based Biomimetic Sensor for the Electronic Detection of Serotonin in Human Blood Plasma", Sensors and Actuators, vol. 171, 2012, pp. 602-610.

* cited by examiner

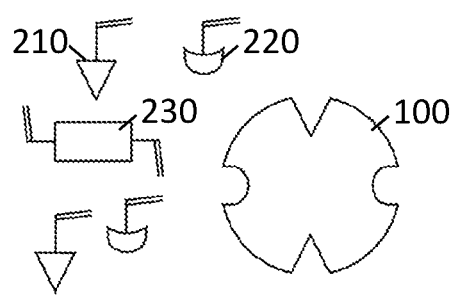
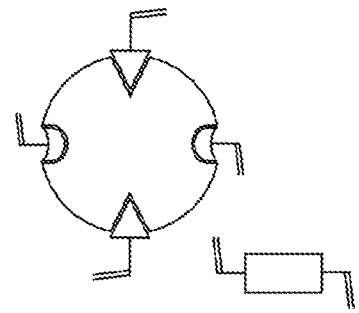
FIG. 1a  FIG. 1b
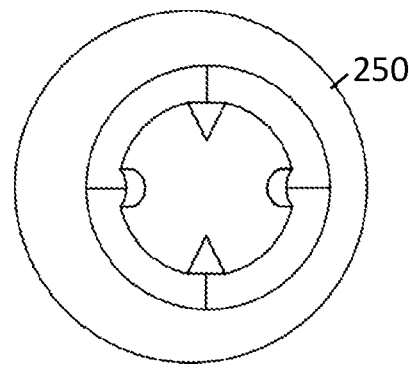
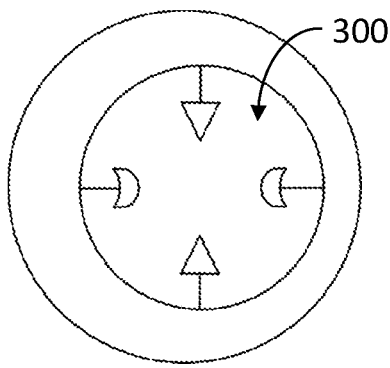
FIG. 1c  FIG. 1d
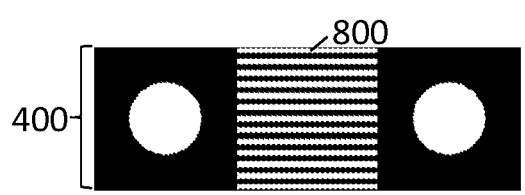
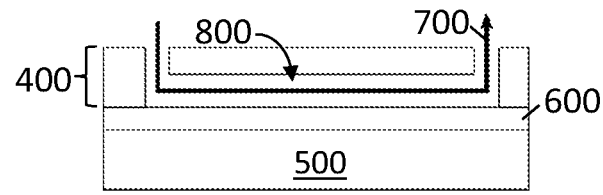
FIG. 2a  FIG. 2b

METHOD FOR IMMOBILIZING MOLECULARLY IMPRINTED POLYMERS

CROSS-REFERENCE TO RELATED APPLICATIONS

The present application is a non-provisional patent application claiming priority to European Patent Application No. 17175655.4, filed Jun. 13, 2017, the contents of which are hereby incorporated by reference.

FIELD OF THE DISCLOSURE

The present disclosure relates to the field of target molecule detection and more in particular to new substrates comprising molecularly imprinted polymers immobilized thereon for detecting target molecules.

BACKGROUND

There is a growing demand for a variety of sensors in the fields of molecular screening, clinical diagnostics, and food- and environmental analysis. Until recently, target molecule quantification in samples was performed in laboratories using analysis techniques such as high-performance liquid chromoatography, that are time consuming, laborious, costly and required stringent conditions and specialized personnel. Therefore, interest in the development of cheaper, reusable, faster and more user friendly sensors is increasing.

In the field of sensors, it is desirable that the quantification of a target molecule in a sample be reliable and consistent. Therefore, much research is focused on techniques for creating stable and reliable sensing substrates in a reproducible way. Issues to be overcome are: stable receptor attachment to the substrate (even in dynamic conditions) and consistency in amount and distribution of the receptors between different sensor substrates. An example sensor may have desirable characteristics such as being cheap, fast, reliable, reusable, and user friendly.

Molecularly imprinted polymers (MIPs) can selectively bind a specific target molecule and can therefore be used as a low-cost and robust alternative to replace the fragile and expensive natural receptors (e.g., antibodies) in molecular sensing devices. However, one challenging issue in using MIPs for sensor development is the lack of simple and cost-effective techniques that allow firm fixation and homogeneous receptor material distribution on the sensor surface.

Peeters et al. (2012) disclosed a differential impedimetric biosensor for the detection of serotonin in human blood plasma (Peeters, Marloes, et al. "MIP-based biomimetic sensor for the electronic detection of serotonin in human blood plasma." Sensors and Actuators B: Chemical 171 (2012): 602-610.). This sensor was based on bulk MIP particles which were immobilized on the transducer substrate using an MDMO-PPV adhesive layer by means of a stamping technique. Nevertheless, there were still several shortcomings that can be improved, such as:

- the variation between different sensor transducer substrates remains relatively high,
- the adhesive used to immobilize the MIPs partially blocks the pores of the MIPs, leading to a reduced sensor sensitivity, and does not withstand dynamic measurements, and
- the synthesis and handling (crushing and washing) of the used bulk MIP particles is time and labor consuming.

Thus, there is still a need for better ways of immobilizing molecularly imprinted polymers on a substrate and making sensors therefrom, which address some or all of the issues outlined above.

SUMMARY

It is an object of the present disclosure to provide good methods for immobilizing molecularly imprinted polymers on a substrate or for using these immobilized molecularly imprinted polymers in sensors.

In example embodiments of the present disclosure, the immobilization is compatible with a variety of substrates.

In example embodiments of the present disclosure, the molecularly imprinted polymers may be firmly grafted to the substrate and can be homogeneously distributed over the grafted area. In Peeters et al., the adhesive layer used for MIP particle immobilization does not assure a stable fixation of the particles during dynamic measurements. Therefore, regeneration of the substrates is not possible. These shortcomings have been at least partially overcome by embodiments of the present disclosure.

In example embodiments of the present disclosure, a low variability between different substrates comprising molecularly imprinted polymers grafted according to embodiments of the present disclosure can be achieved.

In example embodiments of the present disclosure, the molecularly imprinted polymers can be immobilized in a pattern on the substrate, such as in a pattern of lines.

In example embodiments of the present disclosure, the molecularly imprinted polymers can be formed prior to immobilization or simultaneously with the immobilization.

In example embodiments of the present disclosure, the immobilization is achieved in a cost effective way.

In example embodiments of the present disclosure, sensors can be made which are cheap, fast, reliable, reproducible, reusable, highly selective, tunable, upscalable, and/or user friendly.

In example embodiments of the present disclosure, the sensors can be based on a variety of measurement techniques.

In example embodiments of the present disclosure, sensors can be made which are sensitive to a plurality of target molecules.

In a first aspect, the present disclosure relates to a method for immobilizing a molecularly imprinted polymer onto a substrate, comprising:
   a. providing a substrate having an amorphous carbon surface; and
   b. grafting the molecularly imprinted polymer onto the amorphous carbon surface.

In a second aspect, the present disclosure relates to a structure comprising:
   i. a substrate having an amorphous carbon surface provided by an amorphous carbon layer; and
   ii. a molecularly imprinted polymer grafted onto the amorphous carbon surface.

In a third aspect, the present disclosure relates to a use of the structure according to any embodiment of the second aspect for sensing a target molecule.

In a fourth aspect, the present disclosure relates to a method for sensing a target molecule, comprising:
   a. providing a structure according to the second aspect and its embodiments, wherein the molecularly imprinted polymer comprises at least one unoccupied cavity, the cavity being adapted for selectively binding the target molecule;

b. contacting a fluid with the molecularly imprinted polymer, the fluid comprising the target molecule;

c. measuring a signal sensitive to the binding of the target molecule into the at least one empty cavity; and d. optionally comparing the measured signal to a reference value.

Particular aspects of the disclosure are set out in the accompanying independent and dependent claims. Features from the dependent claims may be combined with features of the independent claims and with features of other dependent claims as appropriate and not merely as explicitly set out in the claims.

The present concepts result in the provision of more efficient, stable, and reliable devices of this nature.

The above and other characteristics and features of the present disclosure will become apparent from the following detailed description, taken in conjunction with the accompanying drawings, which illustrate, by way of example, the principles of the disclosure. This description is given for the sake of example only, without limiting the scope of the disclosure. The reference figures quoted below refer to the attached drawings.

BRIEF DESCRIPTION OF THE FIGURES

The above, as well as additional, features will be better understood through the following illustrative and non-limiting detailed description of example embodiments, with reference to the appended drawings.

FIGS. 1a, 1b, 1c, and 1d are schematic representations of the molecularly imprinted polymer synthesis, according to an example embodiment.

FIG. 2a shows a schematic top view of a microfluidic stamp, according to an example embodiment.

FIG. 2b shows a schematic vertical cross-section of the microfluidic stamp on a substrate, according to an example embodiment.

Figure 3:
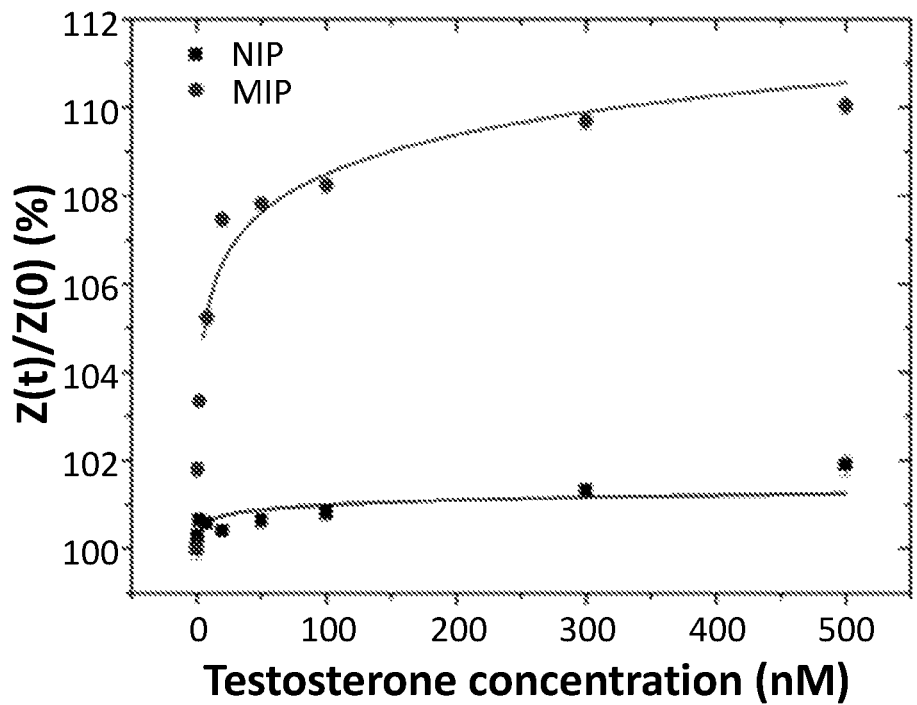
FIG. 3 shows electrochemical impedance spectroscopy dose-response curves of sensors based on molecularly imprinted polymers and based on non-imprinted polymers, exposed to increasing concentrations of testosterone in EtOH/PBS buffer, according to an example embodiment.

In the different figures, the same reference signs refer to the same or analogous elements.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms "first," "second," "third," "fourth" and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms "top," "bottom," "over," "under" and the like in the description and the claims are used for descriptive purposes and not necessarily for describing relative positions. It is to be understood that the terms so used are interchangeable with their antonyms under appropriate circumstances and that the embodiments of the disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

The following terms are provided solely to aid in the understanding of the disclosure.

As used herein, a molecularly imprinted polymer is a polymer structure obtained by polymerizing one or more monomers in the presence of a template molecule, wherein the monomer comprises one or more functional groups for interacting with the template molecule through non-covalent or covalent interactions. By subsequently removing the template molecule, a cavity is left in the polymer structure with a footprint which is specific of the template molecule. In this way, a synthetic receptor is formed which is able to bind a target molecule with high selectivity and specificity; the target molecule being a molecule with the same structure as the template molecule or only minorly differing therefrom. In some embodiments, a plurality of different template molecules may be present during the polymerization. In this way, a molecularly imprinted polymer with different cavities which are specific to different target molecules can be obtained.

As used herein, an amorphous carbon layer or surface relates to a layer or surface consisting of carbon, being amorphous and comprising both $SP^3$ and $SP^2$ carbon atoms. It has localized pi electrons and has dangling bonds. It does not include glassy carbon which is deprived of dangling bonds and is entirely made of $SP^2$ carbon atoms.

In a first aspect, the present disclosure relates to a method for immobilizing a molecularly imprinted polymer onto a substrate, comprising:

a. providing a substrate having an amorphous carbon (a-C) surface; and
b. grafting the molecularly imprinted polymer onto the amorphous carbon surface.

Figure 7:
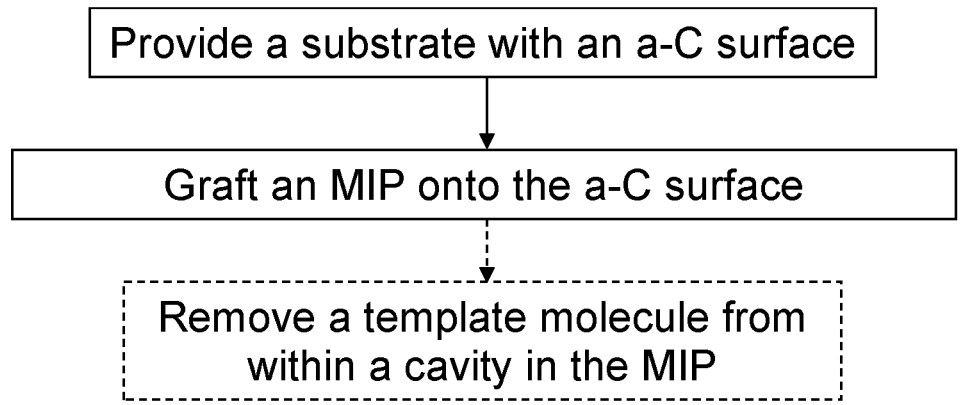
FIG. 7 shows a method for immobilizing a molecularly imprinted polymer onto a substrate, according to an example embodiment.

A flow chart of this method, comprising a further optional step of removing a template molecule from within a cavity in the MIP (cf. infra), is depicted in FIG. 7.

It was surprisingly found within the present disclosure that molecularly imprinted polymers may be directly be grafted covalently onto an amorphous carbon surface. Molecularly imprinted polymers can thus be immobilized on a variety of substrates, simply by providing an amorphous carbon surface on the substrate (if none is present already) and grafting the molecularly imprinted polymer thereto. Typically, the molecularly imprinted polymer used in the present disclosure, when formed ex situ, has unreacted alkenyl groups. When formed in situ, unreacted alkenyl groups are present in the used precursor mixture. Without being bound to a theory, it is believed that amorphous carbon surfaces comprise $SP^2$ carbon atoms involved in double bonds that can react with the unreacted alkenyl groups of the molecularly imprinted polymer to form a covalent bond.

The substrate in the present disclosure can typically be any substrate so long as an amorphous carbon surface can be provided thereon. Typically, the amorphous carbon surface is provided by providing an amorphous carbon layer. In embodiments, step a may comprise providing the amorphous carbon layer by means of a vapor deposition. Other ways to provide the amorphous carbon layer/surface comprise heating up the surface of a crystalline or glassy carbon layer until a top portion of the crystalline or glassy carbon layer is transformed into an amorphous carbon layer. This can be achieved by heating up the complete surface of the crystalline/glassy carbon layer or by heating up specific parts of that surface. Heating up specific parts of that surface can be achieved by applying an electron beam on that surface, e.g., within an electron microscopy set up.

The layer of amorphous carbon may for example be 5 to 50 nm thick, such as 20 nm thick.

In certain embodiments, the amorphous carbon layer may be provided on an H-terminated layer, for example, an H-terminated crystalline carbon layer. An H-terminated layer may allow a good attachment of the amorphous carbon layer thereto.

In embodiments, the substrate may comprise a layer comprising carbon and the amorphous carbon surface may be attached to the layer comprising carbon. The substrate may for example comprise the layer comprising carbon and an amorphous carbon layer formed thereon. Amorphous carbon may form a stable coupling with a layer comprising carbon. In embodiments, the layer comprising carbon may be selected from the list of crystalline materials comprising carbon (e.g. SiC), crystalline materials consisting of carbon (e.g. graphite, graphene, diamond, nanocrystalline diamond, crystalline carbon nanofibers), non-crystalline materials consisting of carbon such as amorphous materials consisting of carbon (diamond-like carbon, amorphous carbon, amorphous carbon nanofibers), amorphous materials comprising carbon (e.g. diamond-like nanocomposites, organic polymers in their amorphous phase), organic polymers in their semi-crystalline phase and glassy carbon (also called glass-like carbon or vitreous carbon). The layer comprising carbon may be a layer consisting of carbon, for example, a layer of a crystalline material consisting of carbon.

When the layer comprising carbon is made of a crystalline or glassy carbon material, the amorphous carbon surface will typically be provided by vapor-depositing a layer of amorphous carbon on the layer comprising carbon or by applying heat or an electron beam on the surface of the layer comprising carbon.

When the layer comprising carbon is already made of an amorphous or semi-crystalline carbon material, the top surface of that layer comprising carbon can directly serve as the amorphous carbon surface or an additional amorphous carbon layer can be provided thereon by a vapor-based method.

In other embodiments, the substrate may comprise a layer selected from the list of SiN, quartz, metal (e.g., Au), glass, and ceramics, and the amorphous carbon surface may be formed by providing an amorphous carbon layer on the layer. The substrate may for example comprise the layer selected from the list of SiN, quartz, metal (e.g., Au), glass, and ceramics, and the amorphous carbon layer comprising the amorphous carbon surface formed on the layer. In addition, a vapor-based method may be used for forming the amorphous carbon layer on the layer selected from the above list. Layers consisting of carbon and especially crystalline layers consisting of carbon are preferred to the layers selected from the list of SiN, quartz, metal (e.g., Au), glass, and ceramics because they are more electrochemically inert, which may be beneficial when used in contact with body fluids or biochemical buffers.

In example embodiments, the layer comprising carbon or the layer selected from the list of SiN, quartz, metal (e.g., Au), glass, and ceramics may have a thickness of from 100 to 300 nm, for instance from 150 to 250 nm.

In example embodiments, the substrate may further comprise a layer of Si or glass. For instance, the substrate may comprise a Si or glass underlayer on which a first layer is formed, the first layer being selected from the layer comprising carbon and the layer selected from the list of SiN, quartz, metal (e.g., Au), glass, and ceramics. The amorphous carbon surface or layer may be formed on that first layer.

In an example embodiment, the substrate may comprise a first layer selected from diamond and nanocrystalline diamond and the amorphous carbon layer (comprising the amorphous carbon surface) formed thereon.

In a first set of embodiments, step b may comprise contacting a precursor mixture of the molecularly imprinted polymer with the amorphous carbon surface and polymerizing the precursor mixture. In embodiments, polymerizing the precursor mixture may comprise exposing the precursor mixture to UV light. In embodiments, the precursor mixture may comprise at least:
  i. a template molecule,
  ii. a first monomer comprising at least two alkenyl groups, and
  iii. a second monomer comprising at least one alkenyl group and at least one functional group capable of interacting with the template molecule;
wherein the first monomer and the second monomer may optionally be a same monomer. The interaction of the functional group with the template molecule can be covalent or non-covalent. In embodiments, the precursor mixture may further comprise a solvent. The in situ formation and simultaneously grafting of the molecularly imprinted polymers may ensure a homogeneous distribution of the molecularly imprinted polymers over the grafted area.

The template molecule may be any molecule one would wish to detect. Typically, the template molecule will be an organic molecule. For example, the template molecule can be a bio-molecule, such as testosterone. In embodiments, the precursor mixture may comprise a plurality of template molecules.

The first monomer comprises at least two alkenyl groups, i.e., at least two reactive double bonds. The first monomer may for example be selected from the list consisting of (meth)acrylate monomers, (meth)acrylamide monomers, styrenic monomers, (meth)acryloyl monomers and cross-linking acrylic monomers (which can be di-, tri- or multi-functional). The first monomer may for example be divinylbenzene which is an example of styrenic monomer having two alkenyl groups, ethylene glycol dimethacrylate which is an example of (meth)acrylate monomer, trimethylolpropane trimethacrylate which is another example of (meth)acrylate monomer, pentaerythritol tetraacrylate which is yet another example of (meth)acrylate monomer, bisacrylamide which is an example of (meth)acrylamide monomer.

The second monomer comprises at least one alkenyl group, i.e., at least one reactive double bond, and at least one functional group capable of interacting with the template molecule. The at least one functional group may for example be selected from the list of —OH, —COOH, —NH$_2$, —N=, —SH, —SO$_3$H, —PO$_3$H, —CN, —CONN—, —COO—, —O—, sulfonate and phosphate groups as well as salts thereof. The second monomer may for example be selected from the list consisting of (meth)acrylate monomers, (meth)acrylamide monomers, styrenic monomers, and (meth)acryloyl monomers. The second monomer may for example be (meth)acrylic acid, acrylamide, 4-vinylpyridine, 2-vinylpyridine, vinyl sulfonic acid, vinyl phosphonic acid, aminoethyl methacrylate hydrochloride, acrylamido-2-methylpropane sulfonic acid and 2-(2'-methacryl oxy-5'-methylphenyl)benzotriazole.

In some embodiments, the first monomer and the second monomer may be the same monomer. Using a single monomer comprising at least two alkenyl groups and at least one functional group capable of interacting with the template molecule may simplify design route, as the need for additional functional monomers and optimization of the relative ratios in the mixture is eliminated. The monomer may for example be pentaerythritol diacrylate, pentaerythritol triacrylate, N,α-bismethacryloyl glycine, or N,O-bismethacryloyl ethanolamine.

In example embodiments, contacting the precursor mixture with the amorphous carbon surface may comprise covering at least part of the amorphous carbon surface with the precursor mixture by a wet coating technique such as spin coating, spray coating, dip coating, drop casting, or printing.

In example embodiments, contacting the precursor mixture with the amorphous carbon surface may comprise providing the precursor mixture in a microfluidic system on top of the amorphous carbon surface. The microfluidic system may be a system comprising any type of structures. The microfluidic system may be a system comprising lane structures (e.g. microfluidic channels), for example, parallel lane structures. Microfluidic systems having any type of structure can be easily made by for instance using electron beam lithography to design a master structure then using the later to form a PDMS microfluidic system. The microfluidic system is placed on the amorphous carbon surface in such a way that the content of the microfluidic channels is in contact with the amorphous carbon surface.

In an example embodiment, a microfluidic system, comprising a substrate on which parallel lanes are formed defining microfluidic channels having a bottom made of the substrate, an open top, an inlet in the substrate for allowing the precursor mixture to get in the channels and an outlet in the substrate for allowing the precursor mixture to get out of the channels, may be placed top down on the amorphous carbon surface thereby forming microfluidic channels having a closed bottom and a closed top (except for the inlet and the outlet). Next, the precursor mixture may be provided in these microchannels via the inlet. The microfluidic system may for example comprise between 20 and 1000 lane structures, such as between 20 to 500 lane structures, such as for instance 75 lane structures. The lane structures may for example have a height of 0.5 to 15 µm, such as of 0.5 to 10 µm, such as for instance 1.75 µm. The lane structures may for example have a length of 5 to 50 µm, such as 10 to 20 µm. The lane structures may for example have a width of 1 to 10 µm, such as 2 to 5 µm. The microfluidic system may for example be an elastomeric stamp such as a polydimethylsiloxane (PDMS) stamp (see example 1a). The microfluidic system may be reusable, such that expensive and time-consuming lithography steps may only be required for making the microfluidic system (as opposed to every time the molecularly imprinted polymers are immobilized). The microfluidic system may be at least partially transparent to electromagnetic radiations suitable for polymerizing the MIPs.

In a second set of embodiments, step b may comprise providing molecularly imprinted polymer particles onto the amorphous carbon surface and grafting the molecularly imprinted polymer particles onto the amorphous carbon surface. In embodiments, the molecularly imprinted polymer particles may comprise unreacted alkenyl groups. The molecularly imprinted polymer particles may be colloidal particles or bulk particles, which may have been formed using a precursor mixture as previously described. Colloidal particles are more homogeneous in size. They can be submicron or not. They can for instance be prepared by emulsion polymerization, for example, miniemulsion polymerization, in which case they tend to have smaller size and submicron particles can be achieved, or by suspension polymerization, in which case they tend have larger sizes and particles larger than 1 µm tend to be formed. The MIPS particles may have a diameter of from 20 nm to 100 microns. However, submicron particles (e.g., from 20 to 500 nm) may be used because they present a larger surface to volume ratio which may be beneficial for interaction with target molecules. In example embodiments, colloidal submicron particles may be used. Grafting the molecularly imprinted polymer particles onto the amorphous carbon surface may comprise photografting the molecularly imprinted polymer particles onto the amorphous carbon surface, e.g., by exposure to UV light.

In example embodiments, providing the molecularly imprinted polymer particles onto the amorphous carbon surface may comprise covering at least part of the amorphous carbon surface with the precursor mixture by a wet coating technique such as spin coating, spray coating, dip coating, drop casting, or printing.

In example embodiments, providing molecularly imprinted polymer particles onto the amorphous carbon surface may comprise providing the molecularly imprinted polymer particles in a microfluidic system on top of the amorphous carbon surface, as was discussed for the first set of embodiments.

In example embodiments, the molecularly imprinted polymer may comprise a template molecule in a cavity therein and the method may further comprise step c, after step b, of:

c. removing the template molecule from within the cavity.

Removing the template molecule from within the cavity may comprise washing the molecularly imprinted polymer. Washing the molecularly imprinted polymer may comprise a plurality of washing steps using different solvent and/or solvent mixtures. The solvent or solvent mixture may comprise one or more of water, ethanol, acetic acid, and methanol. The choice of solvent may be determined by the type of interaction existing between the MIP and the target molecule.

In embodiments, any feature of the first aspect and its embodiments may independently be as correspondingly described for any of the other aspects and their embodiments.

In a second aspect, the present disclosure relates to a structure comprising:
 i. a substrate having an amorphous carbon surface, typically provided by an amorphous carbon layer; and
 ii. a molecularly imprinted polymer grafted onto the amorphous carbon surface.

In example embodiments, the structure may be a structure for sensing a target molecule. The structure may thus be a sensor for sensing a target molecule, such as a biosensor.

In embodiments, the structure may be a sensor and the substrate may be adapted towards a selected measurement method, such as adapted for an impedimetric (e.g. electrochemical impedance spectroscopy), thermal resistance (e.g., a heat transfer method), optical (e.g., surface plasmon resonance), or microgravimetric (e.g., using a quartz crystal microbalance) measurement method.

In embodiments, the structure may be a sensor for sensing a target molecule in a fluid by measuring a change in a property caused thereby, the structure comprising:
 a substrate having an amorphous carbon surface provided by an amorphous carbon layer,
 a molecularly imprinted polymer grafted onto the amorphous carbon surface,
 a flow cell for contacting the molecularly imprinted polymers with the fluid,
 means for measuring a property signal influenced by the presence of the target molecule, and
 a controller system adapted for acquiring the property signal measured by the means.

In example embodiments, the controller system may be further adapted for determining the difference between a property signal determined in presence of the target molecule and a property signal determined in absence of the target molecule. For example, the controller system may be further adapted for determining from this difference a concentration of target molecule in the fluid.

Examples of property signals are impedimetric signals, thermal resistance signals, optical signals or microgravimetric signals.

In some embodiments, the substrate may comprise a layer having a thermal conductivity of at least 80 W/(m·K), for example, at least 100 W/(m·K) measured across its thickness, the layer contacting the amorphous carbon layer. Examples of layers having such a high thermal conductivity are crystalline materials consisting of carbon as mentioned above and metals such as Au, Cu, or Al. The layer having thermal conductivity of at least 80 W/(m·K) may be a multilayer, in which case the thermal conductivity is measured (or calculated) across the thickness of all layers involved. In example embodiments, each of the layers forming the multilayer has a thermal conductivity of at least 80 W/(m·K). For instance, the layer having a thermal conductivity of at least 80 W/(m·K) may be composed of a crystalline material consisting of carbon (contacting the amorphous carbon layer) and a metal layer (contacting the crystalline material consisting of carbon). The thermal conductivity may for example be the thermal conductivity measured under standard conditions, i.e., under atmospheric pressure and at a temperature of 293K. Such a substrate may be suitable for use in a heat transfer method, which measures a thermal resistance (e.g., as described in Peeters, Marloes, et al. "Heat-transfer-based detection of L-nicotine, histamine, and serotonin using molecularly imprinted polymers as biomimetic receptors." *Analytical and bioanalytical chemistry* 405.20 (2013): 6453-6460.).

In embodiments, the structure may be a sensor for sensing a target molecule in a fluid by measuring a change in thermal resistance caused thereby, the structure comprising a substrate having an amorphous carbon surface provided by an amorphous carbon layer and having a layer having a thermal conductivity across its thickness of at least 80 W/(m K) contacting the amorphous carbon layer, a molecularly imprinted polymer grafted onto the amorphous carbon surface, and a heating element contacting the layer having a thermal conductivity of at least 80 W/(m·K).

In embodiments, the structure of the present disclosure may further comprise a first thermocouple adapted to measure a temperature of the layer having a thermal conductivity of at least 80 W/(m·K), and a second thermocouple adapted to measure a temperature above the molecularly imprinted polymer (i.e., at a side opposite the substrate with respect to the molecularly imprinted polymer).

In an example embodiment, the structure may be a sensor for sensing a target molecule in a fluid by measuring a change in thermal resistance caused thereby, the structure comprising:
  a substrate having:
  an amorphous carbon surface provided by an amorphous carbon layer,
  a layer having a thermal conductivity measured across its thickness of at least 80 W/(m K) contacting the amorphous carbon layer,
  a molecularly imprinted polymer grafted onto the amorphous carbon surface,
  a flow cell for contacting the molecularly imprinted polymers with the fluid,
  a first thermocouple for measuring the temperature T1 in the substrate,
  a second thermocouple for measuring the temperature T2 in the fluid above the molecularly imprinted polymer,
  a heating element in contact with the substrate,
  a controller system adapted for:
  acquiring the temperature T1 and the temperature T2 measured by the first and second thermocouples respectively,
  determining a power necessary for maintaining T1 constant,
  feeding the power to the heating element, and
  determining the heat-transfer resistance between the two thermocouples from the temperature T1, the temperature T2 and the power In an example embodiment, the controller system may be further adapted for determining the difference between a heat transfer resistance determined in presence of the target molecule and a heat transfer resistance determined in absence of the target molecule. For example, the controller system may be further adapted for determining from this difference a concentration of target molecule in the fluid.

In other embodiments, the substrate may comprise a nano-crystalline diamond top layer contacting the amorphous carbon surface. The nano-crystalline diamond top layer may be present on a Si layer, such as a Si wafer and both the nano-crystalline diamond top layer and the Si wafer may be doped; the nano-crystalline diamond top layer may be present on a metal layer, such as a Cu layer and the nano-crystalline diamond top layer may be doped. Such substrates may be suitable for use in an electrical conductivity based measurement, such as an electrochemical impedance spectroscopy.

In an embodiment, the structure may be a sensor for sensing a target molecule in a fluid by measuring a change in impedance caused thereby, the structure comprising:
  a substrate having:
  an amorphous carbon surface provided by an amorphous carbon layer,
  an electrically conductive layer contacting the amorphous carbon layer,
  a molecularly imprinted polymer grafted onto the amorphous carbon surface,
  a flow cell for contacting the molecularly imprinted polymers with the fluid,
  a first thermocouple for measuring the temperature T1 in the substrate,
  an optional second thermocouple for measuring the temperature T2 in the fluid above the molecularly imprinted polymer,
  a first electrode electrically connected to the electrically conductive layer,
  a second electrode in the fluid above the molecularly imprinted polymer,
  a heating element in contact with the substrate,
  a controller system adapted for:
  acquiring the temperature T1 and the temperature T2 measured by the first and second thermocouples respectively,
  determining a power necessary for maintaining T1 constant,
  feeding the power to the heating element, and
  determining the impedance between the two electrodes.

In an example embodiment, the controller system may be further adapted for determining the difference between an impedance determined in presence of the target molecule and an impedance determined in absence of the target molecule. For example, the controller system may be further adapted for determining from this difference a concentration of target molecule in the fluid.

Examples of electrically conductive layer layers are crystalline materials consisting of carbon (e.g., doped) as mentioned above, metals such as Au, Cu, or Al, and doped semiconductors such as doped Si. The conductive layer may be a multilayer. For instance, the conductive layer may be composed of a doped crystalline material consisting of carbon (contacting the amorphous carbon layer) and a metal layer or doped semiconductor layer (contacting the crystalline material consisting of carbon).

In embodiments, the molecularly imprinted polymer may comprise at least one cavity, the cavity being adapted for selectively binding a target molecule and optionally comprising the target molecule or a template molecule. The cavity may for example be adapted for binding the target molecule through using the target molecule as template molecule during the synthesis of the molecularly imprinted polymer.

In embodiments, the molecularly imprinted polymer grafted onto the amorphous carbon surface may form a pattern of lines. The pattern of lines may for example be obtained by immobilizing the molecularly imprinted polymer using a microfluidic system comprising lane structures. Molecularly imprinted polymers structured in a pattern of lines may have an increased total surface area, thereby increasing the sensitivity to the target molecule and making it easier to remove the template or target molecules.

In embodiments, any feature of the second aspect and its embodiments may independently be as correspondingly described for any embodiment of the other aspects.

Structures according to the second aspect can be identified for instance by observing a cross section thereof under an electron microscope.

In a third aspect, the present disclosure relates to a use of the structure according to any embodiment of the second aspect for sensing a target molecule.

In embodiments, any feature of the third aspect and its embodiments may independently be as correspondingly described for any embodiment of the other aspects.

In a fourth aspect, the present disclosure relates to a method for sensing a target molecule, comprising:
a. providing a structure according to the second aspect and its embodiments, wherein the molecularly imprinted polymer comprises at least one unoccupied cavity, the cavity being adapted for selectively binding the target molecule;
b. contacting a fluid with the molecularly imprinted polymer, the fluid comprising the target molecule;
c. measuring a signal sensitive to the binding of the target molecule into the at least one empty cavity; and
d. optionally comparing the measured signal to a reference value.

The unoccupied cavity is typically a cavity void of the target molecule or the template molecule, but may for example be filled with solvent molecules.

The fluid may for example be a gas or liquid comprising the target molecule. In embodiments, the fluid may be a solution comprising the target molecule. The fluid may for example comprise a buffer solution, urine, blood or saliva.

The signal sensitive to the binding of the target molecule into the at least one empty cavity may for example be a thermal resistance, impedimetric, optical or microgravimetric signal. In example embodiments, step c may comprise measuring a thermal resistance of the structure. In other embodiments, step c may comprise measuring an impedimetric, optical or microgravimetric signal of the structure.

In embodiments, the molecularly imprinted polymer may comprise a plurality of unoccupied cavities in step a and the signal measured in step c may relate to an amount of the cavities having a target molecule bound therein. The measured signal may for example incrementally, such as linearly, increase based on the number of target molecules bound in the cavities.

In embodiments, any feature of the fourth aspect and its embodiments may independently be as correspondingly described for any embodiment of the other aspects.

The disclosure will now be described by a detailed description of several embodiments of the disclosure. It is clear that other embodiments of the disclosure are possible and contemplated without departing from the scope of the disclosure, the disclosure being limited only by the terms of the appended claims.

Example 1: Synthesis of Molecularly Imprinted Polymers

We now refer to FIGS. 1a-1d, showing a schematic representation of the molecularly imprinted polymer (MIP; 250) synthesis. MIPs (250) were obtained from a precursor mixture comprising a template molecule (100) and one or more monomers (210; 220; 230) (FIG. 1a). The functional groups in the monomers (210; 220) arranged around the template molecule (100) through non-covalent or covalent interactions (FIG. 1b). Subsequently, the monomers (210; 220; 230) were polymerized (250) in the presence of the template molecule (100) (FIG. 1c). After polymerization, the subsequent removal (e.g., by washing) of the template molecule (100) leaves cavities (300) (FIG. 1d). These cavities (300) are complementary to the template molecule (100) in terms of size, shape, and arrangement of the functional groups, allowing the polymer cavities (300) to bind the target molecule with high affinity and specificity.

Example 1a: In Situ Formation of Molecularly Imprinted Polymers Grafted onto a Substrate We now refer to FIG. 2, showing a schematic representation of the structured molecularly imprinted polymer fabrication. In this example, the precursor mixture was provided in a microfluidic stamp on the substrate and polymerized therein.

We now refer to FIG. 2a, showing a schematic top view of a microfluidic stamp (400). In order to obtain such a microfluidic stamp (400), a microfluidic mould was first designed and fabricated as follow. 1 cm×1 cm silicon substrates (L14016, Siegert Wafer GmbH) were thoroughly cleaned and dehydrated by heating them for 5 min at 150° C. The negative photoresist SU-8 2025 (Micro Resist Technology GmbH) was diluted by cyclopentanone from a solid-content of 68.6% to 44.4%. These solutions were spin coated on the Si substrate according the manufacturer's specifications and cured for 2 min at 95° C., resulting in an approximately 4.5 μm thick photoresist layer. The desired pattern (800) of the MIP structures with different widths and heights were designed with the DesignCad lt 2000 software tool. E-beam lithography was performed with a NPGS system (JC Nabity Lithography Systems) mounted on SEM (FEI Quanta 200F). The e-beam line-exposure was set at 0.12 nC/cm with an acceleration voltage of 30 kV. After exposure, the SU-8 layers were baked again for 3 min at 110° C. The substrates were developed with SU-8 developer and rinsed with 2-propanol. The master mold was additionally subjected to a hard-baking step for 2 h at 150° C. to release stress from the resulting SU-8 microstructures and to achieve mechanical stability and durability. The mold can then be reused dozens of times without deteriorating performance.

Subsequently, a cast from the master mold was made in PDMS. The base polymer and curing agent were mixed thoroughly in a 10:1 weight-ratio in a disposable recipient. The introduced air from mixing was removed at an absolute pressure of 0.55 bar for at least 30 min. Next, the uncured PDMS was poured over the mold and subsequently baked in an oven for 3 h at 60° C. The resulting PDMS cast of 2.5 mm high was cut out with a scalpel and peeled off from the mold. The inlet and outlet were cored with a 1 mm biopsy punch and the excess of cured PDMS was removed.

We now refer to FIG. 2b, showing a schematic vertical cross-section of the microfluidic stamp (400) on a substrate (500). Highly doped silicon substrates (resistivity 10-20 kΩ, P-type doping, 10 mm×10 mm×0.525 mm) grown with a<200 nm NCD layer (500; % $CH_4$=4, $PPM_{Boron}$=4800) on top were cleaned by wet etching for 30 min in an oxidizing mixture of boiling potassium nitrate and sulfuric acid (1:10 ratio), followed by washing in an ultrasonic bath with heated ultrapure water. Next, the substrates (500) were thoroughly rinsed with ultrapure water and dried using nitrogen gas. Hydrogenation of the substrates was performed using an ASTeX® reactor equipped with a 2.45 GHz microwave generator: 2 min at 3500 W, 30 Torr, 500 sccm $H_2$ and 5 min at 2500 W, 15 Torr, 500 sccm $H_2$. The substrates (500) were cooled in $H_2$ atmosphere for 40 min. Subsequently, a 20 nm thick amorphous carbon layer (600) was deposited at 40 amperes onto the H-terminated substrates (500) (Leica EM ACE600, carbon thread evaporation).

The fabrication of the MIP structures using polymerization ingredients was optimized to achieve high affinity and selectivity for the target molecule testosterone. The precursor mixture consisted of 0.507 mmol N,O-bismethacryloyl ethanolamine (NOBE; MIP monomer), 0.012 mmol 2,2-dimethoxy-2-phenylacetophenone, 1.088 mmol chloroform and 0.087 mmol testosterone (template molecule).

The microfluidic stamp (400) was placed onto the freshly carbon coated (600) NCD (500) substrate and teflon tubes were connected to the inlet and outlet of the stamp. The precursor mixture was pumped (700) via the inlet through the microfluidic channels (800) until they were all filled. Next, the tubes were removed and the ensemble substrate (500, 600)—stamp (400) with the filled microfluidic channels (800) was placed under UV-light (Lawtronics MESE UV-lamps, 254 nm, 265 mW/cm$^2$). The UV-transmittance of PDMS at 254 nm ranges between 40 and 60%. Polymerization was done for 20 h in the presence of oxygen-free nitrogen purge. After polymerization, the stamp (400) was removed from the substrate (500, 600). The patterned structure consisted of lines of well-defined height (75 lines with a height of 1.75 μm) and a shape defined by the stamp.

The template molecules were removed from the MIP structures by gently shaking the substrate in a mixture of 1:1 ethanol/ultrapure water (7.5 h, 5× solvent change), a mixture of 1:19 acetic acid/methanol (4 h, 2× solvent change), and a mixture of ethanol/ultrapure water (1 h, 4× solvent change).

It was observed that the role of carbon functionalization is crucial to the immobilization of the MIPs, as only hydrogen termination of NCD substrates for photografting was not sufficient to yield a stable immobilization of the MIPs. In the latter case, the bonding of the MIPs was not strong enough to withstand a few washing steps; whereas rigorous multiple washing steps using different solvent and solvent mixtures are typically needed to remove the template.

Example 1b: Grafting of Ex Situ Formed Molecularly Imprinted Polymer Particles onto a Substrate The MIP particles were prepared in accordance Kellens et al. (2016) (Kellens, Evelien, et al. "Improved Molecular Imprinting Based on Colloidal Particles Made from Miniemulsion: A Case Study on Testosterone and Its Structural Analogues." *Macromolecules* 49.7 (2016): 2559-2567.). 2.535 mmol (0.5 g) NOBE, 13.3 nmol (1.46 μg) hydroquinone, 0.447 mmol (0.129 g) testosterone, 91.3 μmol (0.015 g) AIBN and 2.18 mmol (0.26 g) chloroform were mixed to obtain the dispersed phase. For the continuous phase, 0.555 mol (10 g) water was mixed with 0.163 mmol (0.052 g) cetyltrimethyl ammonium chloride (cationic surfactant). Subsequently both phases were added together and ultrasonified (Branson sonifier W450 Digital; ⅛ in. tip) at 0° C. using the following steps: 30% amplitude, 30 s pulse and 20 s pause during a total time of 120 s and 65% amplitude, 30 s pulse and 20 s pause during a total time of 120 s. The obtained emulsion was purged with nitrogen for 2 min and stirred at 750 rpm. For polymerization, the system was illuminated with UV light (Omnicure series lamp with 4 arms) with an iris setting of 20% for the first 2 h and then 3% for 16 h. NIP particles were prepared the same way but without the presence of the target molecule during polymerization. As a following step, the obtained dispersion was filtered to remove large aggregates and the solid content was analyzed gravimetrically. To analyze the diameter and the polydispersity of the miniemulsion particles in water, the dynamic light scattering (DLS, Zeta PALS analyzer of Brookhaven Instruments Corporation, 90° laser detector angle) was used. Transmission electron microscopy (TEM, Tecnai Spirit, FEI, operating at an accelerating voltage of 120 kV in the bright-field imaging mode) was used to visualize the colloidal particles by drop casting them on a carbon coated copper TEM grid (Quantifoil).

On top of a P-type doped silicon wafer (10-20 kΩ resistivity), a 200 nm NCD layer (% $CH_4$=4, $PPM_{Boron}$=4800) was grown. Subsequently, the wafers were washed using a mixture of $KNO_3$ and sulphuric acid (1:10 ratio) at 100° C. for 30 min followed with a rinsing step with water. These substrates were hydrogenated using a microwave generator (2.45 GHz ASTeX reactor) for 2 min at 3500 W, 30 Torr, 500 sccm $H_2$ and 5 min at 2500 W, 15 Torr, 500 sccm $H_2$. Next, an amorphous carbon layer of 20 nm was deposited by evaporation at 40 A (Leica EM ACE600, carbon thread evaporation).

In order to obtain a homogeneous coverage of polymer particles on the functionalized substrates, MIP and NIP particles were redispersed in water and washed with membrane tubes using centrifugation (18 cycles, 2000 rpm, 20 min) to remove the surfactant. Subsequently, the water was replaced by DMSO and the solid content was set to 2 wt. %. This dispersion was then sandwiched between the carbon functionalized NCD substrates and a quartz glass which were separated by a 0.1 mm polydimethylsiloxane spacer. The quartz glass side of this setup was illuminated with UV light (24 h, in nitrogen conditions, Lawtronics MESE UV-Lamps, 254 nm, 265 mW/cm$^2$) to couple the surface vinyl groups of the polymer particles to the amorphous carbon layer on the substrate. After coupling, in order to remove both the target molecules from the imprints of the particles together with any remaining uncoupled particles, the sensor substrates were washed by shaking them in a mixture of 1:1 ethanol/ultrapure water (7.5 h, 5 times), 1:19 acetic acid/methanol (4 h, 2 times) and 1:1 ethanol/ultrapure water (1 h, 4 times). To study the polymer particle distribution on the sensor substrate, scanning electron microscopy (SEM, FEI Quanta 200F) was used.

Figure 8:
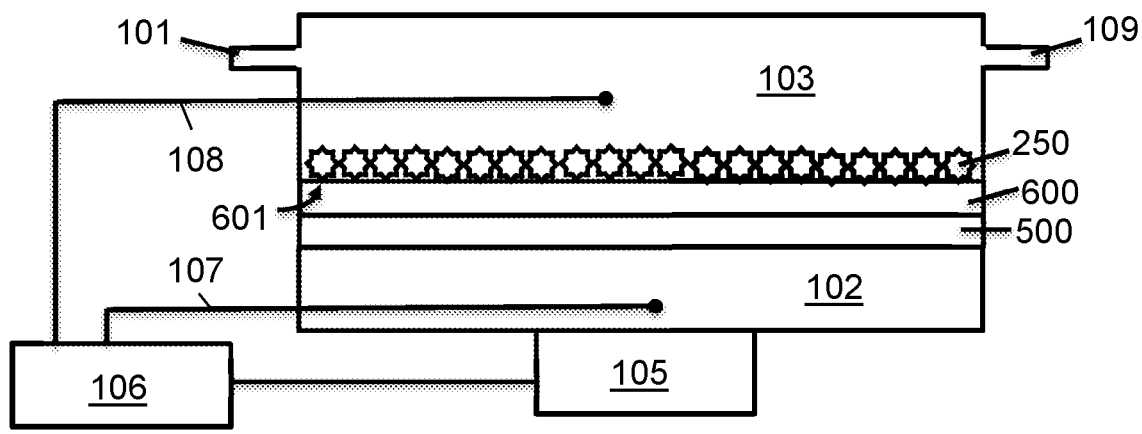
FIG. 8 is a schematic representation of a sensor for sensing a target molecule in a fluid by measuring a change in thermal resistance caused thereby according to an embodiment of the present disclosure, according to an example embodiment.

Example 2: Fabrication of Sensors Based on Molecularly Imprinted Polymers and Sensors Based on Non-Imprinted Polymers Using a substrate adapted to a particular measurement technique and one of the methods described in example 1a or 1b, a sensor based on MIPs can be made. The substrate of example 1a comprising NCD on a highly doped Si wafer is for example suitable for use in electrochemical impedance spectroscopy (EIS). Alternatively, a substrate comprising a copper layer can for instance be used to form a sensor suitable for use in a heat transfer method. This embodiment is shown in FIG. 8.

Example 2a: Sensors Based on In Situ Formation of Molecularly Imprinted Polymers Grafted onto a Substrate EIS sensors based on MIPs were made as outlined in example 1a.

EIS sensors comprising non-imprinted polymer (NIP) lanes were synthesized in the same manner as the MIP structures in example 1a, but in the absence of the template molecules. These NIP lanes were used as a negative control in example 3a. The NIP was washed in the same way as the MIP.

Example 2b: Sensors Based on the Grafting of Ex Situ Formed Molecularly Imprinted Polymer Particles onto a Substrate EIS sensors based on MIPs were made as outlined in example 1b.

EIS sensors based non-imprinted polymer (NIP) particles were synthesized in the same manner as the MIP structures in example 1b, but in the absence of the template molecules. These NIPs were used as a negative control in example 3b. The NIP was washed in the same way as the MIP.

Example 3: Comparison Between Sensors Based on Molecularly Imprinted Polymers and Sensors Based on Non-Imprinted Polymers

Example 3a: Comparison Between Sensors Based on In Situ Formed MIP and NIP

Electrochemical Impedance Spectroscopy (EIS) was used as an electronic-read out tool to compare sensors based on MIPs and sensors based on NIPs obtained in example 2a. The measurements were executed using a custom designed differential impedance sensor-cell set-up which can measure both MIP and NIP substrates simultaneously thereby eliminating the influence of the surroundings (such as temperature fluctuations) and sample variations (such as different biological residue content). The flow-through cell had an internal volume of 300 μL and was made of polymethyl methacrylate. All measurements were temperature controlled using a proportional integral derivative controller (P=5, I=8, D=0). The MIP- and NIP-coated electrodes were installed symmetrically with respect to a gold wire serving as a common counter electrode. The contact area of each electrode with the liquid was defined by O-rings (28 mm$^2$), and the distance from the sensing substrates to the counter electrode was 1.7 mm. Two other (ground) electrodes are present on the copper block of each substrate. The impedance signals were measured in a frequency range of 100 Hz to 100 kHz with 10 frequencies per decade and a scanning speed of 5.69 s per sweep. The amplitude of the alternating current voltage was fixed to 10 mV under open circuit conditions. Silver paste was used to improve the contact between the transducer substrate and the copper blocks.

The binding behavior of the MIP and NIP structures for testosterone was tested using EIS at the physiological pH (7.4) and temperature (37° C.). Testosterone solutions were prepared using ethanol/aqueous media mixtures as the former had limited solubility in water. For these experiments, a mix of ethanol and 1×PBS solution, filtered urine or saliva (in a 20/80 wt. % ratio, passed through Chromafil filters for polar media, pore size 1 and 5 μm) was spiked with testosterone to obtain the following target molecule concentrations: 0.5, 2, 8, 20, 50, 100, 300 and 500 nM. Subsequently, the sensor substrates were integrated in the differential sensor set-up and the impedance signal was allowed to stabilize in the ethanol/buffer or urine or saliva solution containing no target or analogues molecules (blank sample). After stabilization, 1 mL of the spiked samples were added, from low to high concentration with 15 minute intervals. To obtain the dose-response graphs, the mean impedance value of the last 35 data points obtained after administration of a certain concentration (Z(t)) was normalized with the initial impedance stabilization value (blank sample, Z(0)). The obtained value was plotted against that specific testosterone concentration. To test the cross-selectivity, impedance measurements were conducted for the structural analogues β-estradiol and estriol using the following concentrations: 0.5, 2, 8, 20, 50 and 100 nM.

We now refer to FIG. 3. The dose-response curves for sensor in the buffer solution shows that there was a significant difference in sensor response between the MIP (dots) and NIP (squares) functionalized substrates and clearly indicates that the MIP is specifically binding the target molecule. The highest added testosterone concentration (500 nM) resulted in an increase of the impedance signal with 10.03±0.19% for the MIP and 1.89±0.23% for the NIP. Even the addition of the lowest testosterone concentration (0.5 nM) led to a measurable increase in the MIP signal of 1.8±0.15%. In addition, the sensor substrate can also be regenerated by using the same washing protocol as used to remove the template testosterone molecules (using the same flow cell or outside of the cell).

Figure 4:
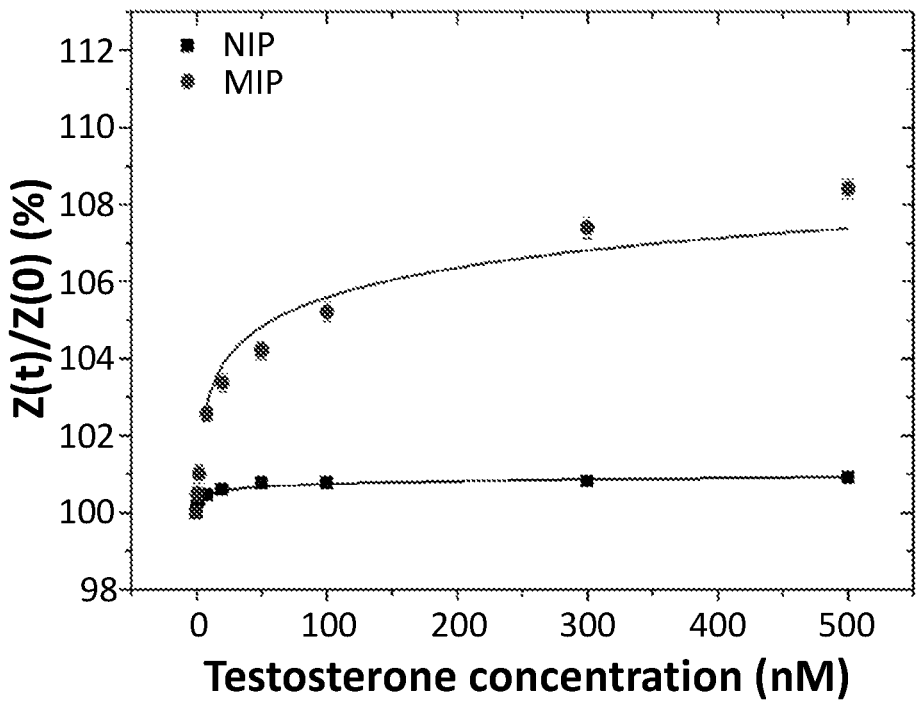
FIG. 4 shows electrochemical impedance spectroscopy dose-response curves of regenerated sensors based on molecularly imprinted polymers and based on non-imprinted polymers, exposed to increasing concentrations of testosterone in EtOH/PBS buffer, according to an example embodiment.

We now refer to FIG. 4. As a proof for regeneration, the substrates that were used to construct the previous graph were subsequently washed for a second time with solvent mixtures to remove both aspecifically and specifically bound testosterone from the polymers. The polymer structures remained intact after washing when observed with the optical microscope. The dose-response curves obtained with these substrates are shown in FIG. 4. From this figure, it can be seen that the MIP structures (dots) are still capable of binding a high amount of testosterone in comparison to the NIP structures (squares), even after regeneration. When the highest concentration of testosterone is added (500 nM), the impedance signal increases 8.40±0.26% for the MIP and 0.90±0.09% for the NIP. However, these values are not as high as the values obtained from the previous sensor measurement. This effect can be due to incomplete testosterone removal after the second washing procedure, which can be easily overcome by extending the time of washing or otherwise optimizing the protocol for removal of the target molecules from the cavities.

Figure 5:
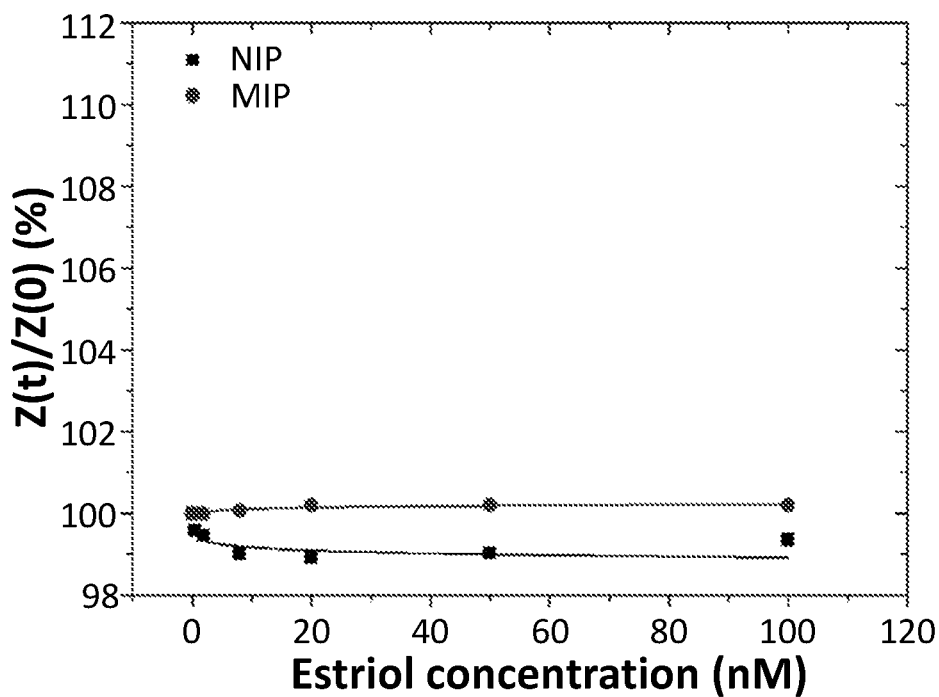
FIG. 5 shows electrochemical impedance spectroscopy dose-response curves of sensors based on molecularly imprinted polymers and based on non-imprinted polymers, exposed to increasing concentrations of estriol in EtOH/PBS buffer, according to an example embodiment.

We now refer to FIG. 5. To test the selectivity of these MIP structures, EIS measurements where testosterone was replaced with a structurally similar but nevertheless differently functionalized molecule, estriol, was performed. The same polymer structure dimensions (75 polymer lines with a height of 1.75 μm) and read-out set-up (differential cell and EIS) were used. The dose-response curves for the MIP (dots) and NIP (squares) functionalized substrates exposed to increasing concentrations of estriol is shown in FIG. 5. It can be clearly seen that estriol is not binding at all to the MIP or NIP structures. A concentration of 100 nM resulted in an increase of the impedance signal of the MIP with 0.19±0.12% for estriol. Similar experiments, but replacing estriol with β-estradiol which is structurally closer to testosterone than estriol is, were also performed and results following a similar trend were obtained.

Figure 6:
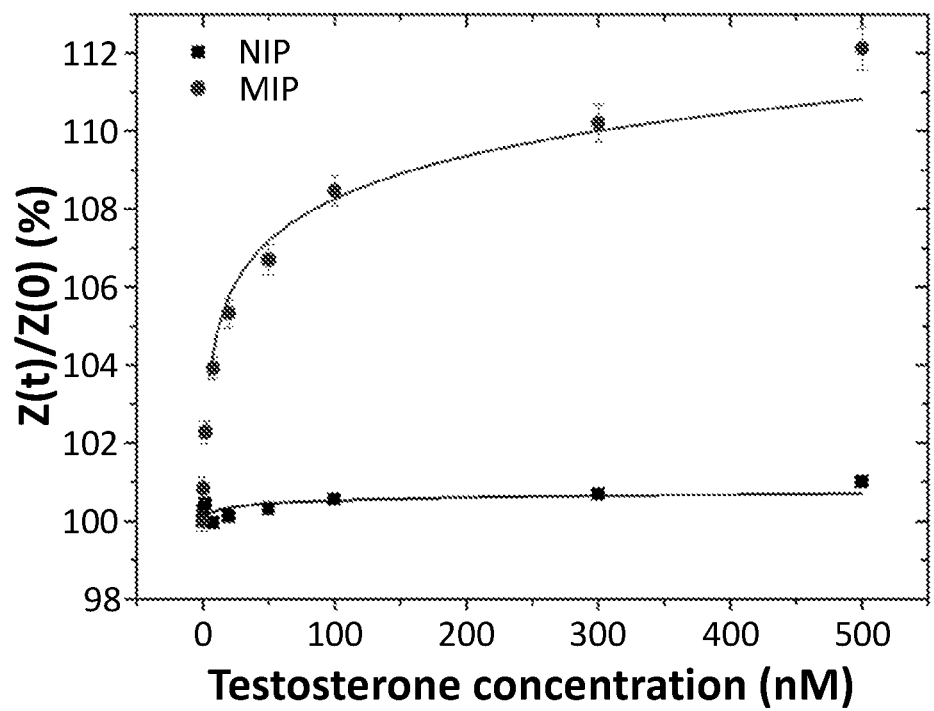
FIG. 6 shows electrochemical impedance spectroscopy dose-response curves of sensors based on molecularly imprinted polymers and based on non-imprinted polymers, exposed to increasing concentrations of testosterone in EtOH/urine solution, according to an example embodiment.

We now refer to FIG. 6. After obtaining a selective response from the MIP structures in testosterone spiked EtOH/PBS buffer solutions, the same experiments were performed with testosterone-spiked solutions where the PBS buffer was replaced with urine. This urine was obtained from a healthy volunteer and, as a preparation step, it was filtered in order to remove large structures (any residual cells and other large impurities). This way, the binding characteristics of the MIP (dots) and NIP (squares) structures can be analyzed in the presence of other molecules such as hormones, vitamins, proteins, etc. which are present in real patient samples. The maximum impedance increase of the NIP and MIP after adding a concentration of 500 nM testosterone were 0.99±0.09% and 12.11±0.53% respectively. At the lowest testosterone concentration of 0.5 nM, the MIP gave a response of 0.84±0.29%. These results show that even in complex real patient samples, the MIP structure is still able to detect testosterone in a specific way. Similar experiments, but replacing urine with saliva, were also performed and results following a similar trend were obtained.

Example 3b: Comparison Between Sensors Based on the Grafting of Ex Situ Formed MIP and NIP Analogous experiments as outlined in example 3a were performed on the sensors obtained in example 2b and analogous results were obtained.

Example 4: Heat Transfer Method Sensor Based on Molecularly Imprinted Polymers

FIG. 8 shows a heat transfer sensor comprising a structure according to the present disclosure. A substrate (102, 500, 600) is provided comprising a copper substrate (102), a nano-crystalline diamond layer (500) provided on the copper substrate, and an amorphous carbon layer (600) provided on the nano-crystalline diamond layer (500), thereby providing the amorphous carbon surface (601). MIPs (250) are grafted on the top surface of the amorphous carbon layer (600). A heating element (105) (power resistor of 22 ohms, MPH20S, Farnell, Grace-Hollogne, Belgium) is present in contact with the copper substrate (102). The nano-crystalline diamond layer (500) and the amorphous carbon layer (600) can be heated by means of the copper substrate (102) by means of a heating element (105). The temperature T1 of the substrate (102, 500, 600), and in particular of the copper substrate (102) is measured by a first thermocouple (107) (type K, diameter 500 TC Direct, Nederweert, The Netherlands) and the temperature T1 of the copper substrate (102) is maintained at the constant temperature of 37.00±0.02° C. with a controller system (106). The temperature in a liquid flow cell (103) above the MIPs (250) is monitored in time via a second thermocouple (108). The liquid flow cell (103) has an inlet (101) and an outlet (109) for fluid permitting to flush the cell with buffer or to introduce a sample therein. The controller system (106) is adapted for acquiring the temperatures T1 and T2 via the presence of a data acquisition unit (Picolog TC08, Picotech, United Kingdom). The controller system (106) is further adapted for determining the output power P necessary for maintaining T1 constant via the presence of a PID controller. The controller system (106) is further adapted for feeding the output power P to the heating element (105) via a second controller (NI USB 9263, National Instruments, USA) and a power operational amplifier (LM675, Farnell, Belgium). The controller system (106) is further adapted for determining the heat-transfer resistance $R_{th}=(T1-T2)/P$ via a computer.

During each measurement, the temperature in the copper substrate (102) is kept constant at 37° C.±0.02° C. Each measurement is performed in absence of flow.

To start a measurement, the setup is filled with a buffer solution and is allowed to heat up to 37.00±0.02° C. and left to stabilize. After stabilization, the heat-transfer resistance is computed. Then, the sample comprising the target molecule is introduced by the inlet (101) and replaces the buffer which is evacuated by the outlet (109). The target molecule now binds to the MIPs (250) and the liquid that was present in these binding cavities (300) is now replaced with the target molecule, which has a different thermal resistance than the liquid it replaces. As a result, the overall thermal resistance of the sensor substrate+MIPs (102, 500, 600, 250) will change depending on how much target molecules are bound, resulting in changes in temperature T2 of the fluid. After calculating the power P necessary to keep the T1 constant, this value can then be used to obtain the thermal resistance Rth as follow: $R_{th}=(T1-T2)/P$, in which Rth is the thermal resistance, P is the power in watt, T1 is the temperature in degrees Celsius of the copper substrate and T2 is the temperature in degrees Celsius of the fluid. The change in thermal resistance between the substrate+MIPs in presence of buffer and the substrate+MIPs in presence of the sample can then be correlated with the amount of target molecule captured by the MIPs and hence the concentration of target molecule in the sample.

It is to be understood that although example embodiments, specific constructions and configurations, as well as materials, have been discussed herein for devices according to the present disclosure, various changes or modifications in form and detail may be made without departing from the scope and technical teachings of this disclosure. For example, any formulas given above are merely representative of procedures that may be used. Functionality may be added or deleted from the block diagrams and operations may be interchanged among functional blocks. Steps may be added or deleted to methods described within the scope of the present disclosure.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A method for immobilizing a molecularly imprinted polymer onto a substrate, comprising:
    (a) providing a substrate having an amorphous carbon surface; and
    (b) grafting the molecularly imprinted polymer directly onto the amorphous carbon surface,
    wherein step (b) comprises:
    contacting a precursor mixture of the molecularly imprinted polymer with the amorphous carbon surface; and
    polymerizing the precursor mixture by exposure to UV light.

2. The method according to claim 1, wherein step (a) comprises providing an amorphous carbon layer by vapor deposition.

3. The method according to claim 1, wherein the precursor mixture comprises:
    a template molecule;
    a first monomer comprising at least two alkenyl groups; and a second monomer comprising at least one alkenyl group and at least one functional group capable of interacting non-covalently with the template molecule,
wherein the first monomer and the second monomer are optionally a same monomer.

4. The method according to claim 3, wherein contacting the precursor mixture with the amorphous carbon surface comprises providing the precursor mixture in a microfluidic system on top of the amorphous carbon surface.

5. The method according to claim 1, wherein contacting the precursor mixture with the amorphous carbon surface comprises covering at least part of the amorphous carbon surface with the precursor mixture by a wet coating technique.

6. The method according to claim 1, wherein step (b), comprises:
providing molecularly imprinted polymer particles onto the amorphous carbon surface; and
grafting the molecularly imprinted polymer particles onto the amorphous carbon surface.

7. The method according to claim 1, wherein the molecularly imprinted polymer comprises a template molecule in a cavity therein and wherein the method further comprises step (c) after step (b), of:
(c) removing the template molecule from within the cavity.

8. The method according to claim 3, wherein the molecularly imprinted polymer comprises a template molecule in a cavity therein and wherein the method further comprises step (c), after step (b), of:
(c) removing the template molecule from within the cavity.

9. The method according to claim 6, wherein the molecularly imprinted polymer comprises a template molecule in a cavity therein and wherein the method further comprises step (c), after step (b) of:
c) removing the template molecule from within the cavity.

10. A structure comprising:
a substrate having an amorphous carbon surface provided by an amorphous carbon layer; and
a molecularly imprinted polymer directly grafted onto the amorphous carbon surface.

11. The structure according to claim 10, wherein the molecularly imprinted polymer comprises at least one cavity, the at least one cavity being adapted for selectively binding a target molecule and optionally comprising the target molecule or a template molecule.

12. The structure according to claim 10, wherein the molecularly imprinted polymer grafted onto the amorphous carbon surface forms a pattern of lines.

13. The structure according to claim 10, wherein the substrate comprises a layer having a thermal conductivity measured across a thickness of at least 80 W/(m K) contacting the amorphous carbon layer.

14. The structure according to claim 10, wherein the substrate further comprises a layer comprising carbon.

15. The structure according to claim 14, wherein the amorphous carbon surface is attached to the layer comprising carbon.

16. The structure according to claim 13, being a sensor for sensing a target molecule in a fluid by measuring a change in thermal resistance caused thereby, the structure further comprising:
a flow cell for contacting the molecularly imprinted polymer with the fluid;
a first thermocouple for measuring a temperature T1 in the substrate;
a second thermocouple for measuring a temperature T2 in the fluid above the molecularly imprinted polymer;
a heating element in contact with the substrate;
a controller system adapted for:
acquiring the temperature T1 and the temperature T2 measured by the first and second thermocouples respectively;
determining a power necessary for maintaining the temperature T1 constant;
feeding the power to the heating element; and
determining a heat-transfer resistance between the two thermocouples from the temperature T1, the temperature T2, and the power.

17. A method for sensing a target molecule, comprising:
(a) providing a structure according to claim 10, wherein the molecularly imprinted polymer comprises at least one unoccupied cavity, the unoccupied cavity being adapted for selectively binding the target molecule;
(b) contacting a fluid with the molecularly imprinted polymer, the fluid comprising the target molecule;
(c) measuring a signal sensitive to a binding of the target molecule into the at least one unoccupied cavity; and
(d) optionally comparing the measured signal to a reference value.

18. The method according to claim 17, wherein step (c) comprises measuring a thermal resistance of the structure.

19. The method according to claim 17, wherein the molecularly imprinted polymer comprises a plurality of unoccupied cavities in step (a) and wherein the signal measured in step (c) relates to an amount of the at least one unoccupied cavity having a target molecule bound therein.

20. A method for immobilizing a molecularly imprinted polymer onto a substrate, comprising:
(a) providing a substrate having an amorphous carbon surface; and
(b) grafting the molecularly imprinted polymer onto the amorphous carbon surface,
wherein step (b) comprises:
contacting a precursor mixture of the molecularly imprinted polymer with the amorphous carbon surface; and
polymerizing the precursor mixture, and
wherein contacting the precursor mixture with the amorphous carbon surface comprises providing the precursor mixture in a microfluidic system on top of the amorphous carbon surface.

21. A structure comprising:
a substrate having an amorphous carbon surface provided by an amorphous carbon layer; and
a molecularly imprinted polymer grafted onto the amorphous carbon surface, wherein the molecularly imprinted polymer grafted onto the amorphous carbon surface forms a pattern of lines.

* * * * *